United States Patent [19]

Ertl et al.

[11] Patent Number: 4,689,416
[45] Date of Patent: Aug. 25, 1987

[54] PROCESS FOR THE PREPARATION OF 1-OXA-3,8-DIAZA-4-OXO-SPIRO(4.5)DECANE COMPOUNDS

[75] Inventors: Josef Ertl, Wertingen; Hartmut Wiezer, Eppstein/Taunus, both of Fed. Rep. of Germany

[73] Assignee: Hoechst Aktiengellschaft, Fed. Rep. of Germany

[21] Appl. No.: 883,170

[22] Filed: Jul. 8, 1986

[30] Foreign Application Priority Data

Jul. 10, 1985 [DE] Fed. Rep. of Germany ....... 3524543

[51] Int. Cl.[4] .......................................... C07D 498/10
[52] U.S. Cl. .......................................... 546/19; 524/99
[58] Field of Search .......................................... 546/19

[56] References Cited
FOREIGN PATENT DOCUMENTS 2933732 3/1981 Fed. Rep. of Germany ........ 546/19
3149453 8/1982 Fed. Rep. of Germany ........ 546/19
3523679 1/1986 Fed. Rep. of Germany ........ 546/19

Primary Examiner—Robert T. Bond
Attorney, Agent, or Firm—Connolly and Hutz

[57] ABSTRACT

The reaction for the preparation of 1-oxa-3,8-diaza-4-oxo-spiro[4.5]decane compounds of the formula

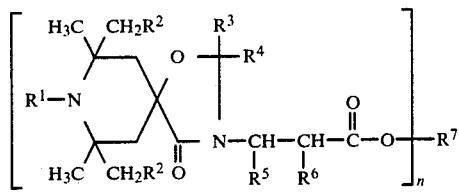

proceeds more rapidly and more completely if it is performed in the presence of a phase transfer catalyst in an aromatic hydrocarbon which is liquid at room temperature.

6 Claims, No Drawings

PROCESS FOR THE PREPARATION OF 1-OXA-3,8-DIAZA-4-OXO-SPIRO(4.5)DECANE COMPOUNDS

The invention relates to a process for the preparation of 1-oxa-3,8-diaza-4-oxo-spiro[4.5]decane compounds which can be used as light stabilizers for polymers or as intermediate products for the preparation of plastic-material additives.

Compounds of the formula

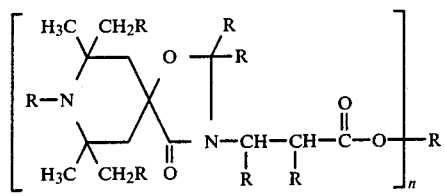

are known (cf. German Offenlegungsschrift No. 3,149,453). However, the process for preparing them is complicated since during the reaction the reaction-medium is changed several times, which necessitates additional extractions and distillations.

It has now been found that the preparation reaction proceeds more rapidly and more completely if an aromatic hydrocarbon, liquid at room temperature, is used as solvent and a phase transfer catalyst is added.

The subject of the invention is therefore a process for the preparation of 1-oxa-3,8-diaza-4-oxo-spiro[4.5]decane compounds of the formula I

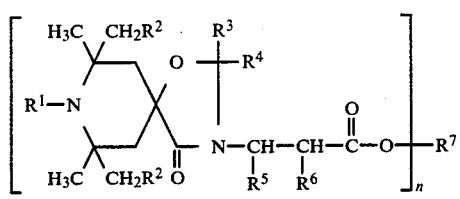

wherein n is an integer from 1 to 4, $R^1$ is hydrogen, $C_1$-$C_4$ alkyl, benzyl, allyl, $C_2$-$C_{30}$ alkanoyl, $C_3$-$C_{20}$ alkenoyl, $C_7$-$C_{11}$ aroyl, $C_8$-$C_{14}$ arylalkanoyl or $C_8$-$C_{20}$ alkylaryl, $R^2$ denotes hydrogen or $C_1$-$C_4$ alkyl, $R^3$ is hydrogen, $C_1$-$C_{18}$ alkyl, $C_5$-$C_{12}$ cycloalkyl, a phenyl or naphthyl group which may be substituted by chlorine or $C_1$-$C_4$ alkyl, or a $C_7$-$C_{12}$ phenylalkylene group optionally substituted by $C_1$-$C_4$ alkyl, $R^4$ denotes hydrogen, $C_1$-$C_4$ alkyl, $C_5$-$C_{12}$ cycloalkyl, $C_1$-$C_3$ alkenyl substituted by —COOH, carb(-$C_1$-$C_4$alkoxy) or carbamoyl, a phenyl, naphthyl or pyridyl group which may be substituted by $C_1$-$C_4$ alkoxy or $C_1$-$C_4$ alkyl, or a $C_7$-$C_{12}$ phenylalkyl group which may be substituted by $C_1$-$C_4$ alkyl, or $R^3$ and $R^4$ together with the carbon atom which binds them may form a cycloalkyl group which may be substituted by one to four $C_1$-$C_4$ alkyl groups, or a radical of formula II

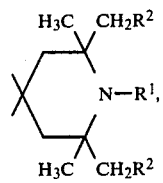

wherein $R^1$ and $R^2$ have the abovementioned meaning, $R^5$ is hydrogen, methyl, phenyl or carb($C_1$-$C_{21}$ alkoxy), $R^6$ denotes hydrogen or methyl, $R^7$ denotes, for n=1, hydrogen, $C_1$-$C_{21}$ alkyl, $C_2$-$C_{22}$ alkenyl, $C_7$-$C_{18}$ phenylalkyl, $C_5$-$C_{12}$ cycloalkyl, phenyl, naphthyl, $C_7$-$C_{18}$ alkylphenyl, a radical of the formula

in which $R^1$ and $R^2$ have the meaning specified above, $C_2$-$C_{20}$ alkyl which is interrupted by —O— or $$-\underset{R^8}{\underset{|}{N}}-$$

and/or substituted by a radical of the formula III

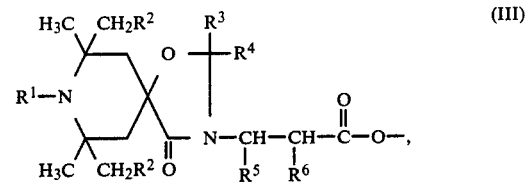

or by the $C_1$-$C_{21}$ alkylcarboxyl, $R^1$, $R^2$, $R^3$, $R^4$, $R^5$ and $R^6$ having the meaning specified above and $R^8$ being hydrogen or $C_1$-$C_{10}$ alkyl, $R^7$ denotes, for n=2, straight-chain or branched $C_1$-$C_{30}$ alkylene, $C_2$-$C_{30}$ alkenylene, phenyldialkylene, it being possible for these radicals to be interrupted by —O— or $$-\underset{R^8}{\underset{|}{N}}-,$$

wherein $R^8$ has the meaning specified above, $R^7$ denotes, for n=3 or 4, a radical of the formulae IV, V, VI or VII

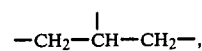

(IV)

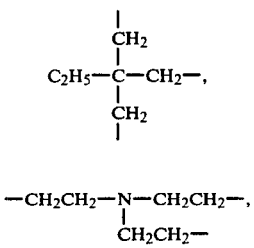

(V)

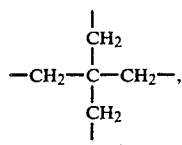

(VI)

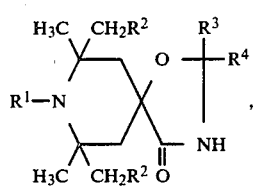

(VII)

by reaction of compounds of the formula VIII

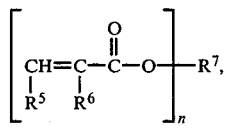

(VIII)

with compounds of the formula IX $$\left[ \begin{array}{c} CH=C-\overset{O}{\overset{\|}{C}}-O \\ | \quad | \\ R^5 \quad R^6 \end{array} \right]_n R^7,$$

(IX)

where n, $R^1$, $R^2$, $R^3$, $R^4$, $R^5$, $R^6$ and $R^7$ have the above-mentioned meaning, in an inert solvent at a temperature of 30° to 150° C. in the presence of a basic catalyst, wherein the reaction is performed in the presence of 0.05 to 20 mol %, referred to the compound VIII, of a phase transfer catalyst in an aromatic hydrocarbon which is liquid at room temperature.

$R^1$ is preferably hydrogen, $C_1$–$C_4$ alkyl, $C_2$–$C_{18}$ alkanoyl, for example methyl, ethyl, propyl, butyl, acetyl, propionyl, butyryl, lauroyl, stearoyl, particularly preferably hydrogen or one of the said acid radicals. In particular $R^1$ is hydrogen.

$R^2$ is preferably hydrogen or $C_1$–$C_4$ alkyl, for example methyl, ethyl, propyl, butyl. In particular $R^2$ is hydrogen.

$R^3$ and $R^4$ are, independently of each other, $C_1$–$C_{18}$ alkyl, $C_5$–$C_{12}$ cycloalkyl or phenyl, for example ethyl, butyl, octyl, lauryl, stearyl, cyclohexyl, cyclodecyl, particularly preferably $C_1$–$C_7$ alkyl. In particular $R^3$ and $R^4$ are $C_1$–$C_4$ alkyl, for example methyl.

$R^3$ and $R^4$ together with the carbon atom which binds them are preferably $C_5$–$C_{12}$ cycloalkylene, particularly preferably $C_6$- or $C_{12}$-cycloalkylene, in particular cyclododecylene.

$R^5$ is preferably hydrogen, methyl or phenyl, particularly preferably hydrogen.

$R^6$ is preferably hydrogen or methyl. In particular $R^6$ is hydrogen.

$R^7$ is $C_1$–$C_{21}$ alkyl, straight-chain or branched $C_1$–$C_{30}$ alkylene, for example methyl, butyl, octyl, lauryl, stearyl, ethylene, butylene, hexylene, particularly preferably $C_1$–$C_{15}$ alkyl. In particular $R^7$ is $C_{12}$–$C_{14}$ alkyl, for example lauryl.

Suitable compounds of the formula VIII are, for example, 2-butyl-7,7,9,9-tetramethyl-1-oxa-3,8-diaza-4-oxo-spiro[4.5]decane 2-isobutyl-7,7,9,9-tetramethyl-1-oxa-3,8-diaza-4-oxo-spiro[4.5]decane 2-pentyl-7,7,9,9-tetramethyl-1-oxa-3,8-diaza-4-oxo-spiro[4.5]decane 2-isopentyl-7,7,9,9-tetramethyl-1-oxa-3,8-diaza-4-oxo-spiro[4.5]decane 2-hexyl-7,7,9,9-tetramethyl-1-oxa-3,8-diaza-4-oxo-spiro[4.5]decane 2-heptyl-7,7,9,9-tetramethyl-1-oxa-3,8-diaza-4-oxo-spiro[4.5]decane 2-isoheptyl-7,7,9,9-tetramethyl-1-oxa-3,8-diaza-4-oxo-spiro[4.5]decane 2-nonyl-7,7,9,9-tetramethyl-1-oxa-3,8-diaza-4-oxo-spiro[4.5]decane 2-isononyl-7,7,9,9,tetramethyl-1-oxa-3,8-diaza-4-oxo-spiro[4.5]decane 2-undecyl-7,7,9,9-tetramethyl-1-oxa-3,8-diaza-4-oxo-spiro[4.5]decane 2-phenyl-7,7,9,9-tetramethyl-1-oxa-3,8-diaza-4-oxo-spiro[4.5]decane 2-(4-chlorophenyl)-7,7,9,9-tetramethyl-1-oxa-3,8-diaza-4-oxo-spiro[4.5]decane 2-ethyl-2,7,7,9,9-pentamethyl-1-oxa-3,8-diaza-4-oxo-spiro[4.5]decane 2-propyl-2,7,7,9,9-pentamethyl-1-oxa-3,8-diaza-4-oxo-spiro[4.5]decane 2-isopropyl-2,7,7,9,9-pentamethyl-1-oxa-3,8-diaza-4-oxo-spiro[4.5]decane 2-butyl-2,7,7,9,9-pentamethyl-1-oxa-3,8-diaza-4-oxo-spiro[4.5]decane 2-isobutyl-2,7,7,9,9-pentamethyl-1-oxa-3,8-diaza-4-oxo-spiro[4.5]decane 2-pentyl-2,7,7,9,9-pentamethyl-1-oxa-3,8-diaza-4-oxo-spiro[4.5]decane 2-hexyl-2,7,7,9,9-pentamethyl-1-oxa-3,8-diaza-4-oxo-spiro[4.5]decane 2-nonyl-2,7,7,9,9-pentamethyl-1-oxa-3,8-diaza-4-oxo-spiro[4.5]decane 2,2,7,7,9,9-hexamethyl-1-oxa-3,8-diaza-4-oxo-spiro[4.5]decane 2,2,7,7,8,9,9-heptamethyl-1-oxa3,8-diaza-4-oxo-spiro[4.5]decane 2,2-diethyl-7,7,9,9-tetramethyl-1-oxa-3,8-diaza-4-oxo-spiro[4.5]decane 2,2-dipropyl-7,7,9,9-tetramethyl-1-oxa-3,8-diaza-4-oxo-spiro[4.5]decane 2,2-dibutyl-7,7,9,9-tetramethyl-1-oxa-3,8-diaza-4-oxo-spiro[4.5]decane 2-ethyl-2-pentyl-7,7,9,9-tetramethyl-1-oxa-3,8-diaza-4-oxo-spiro[4.5]decane 2,2-dibenzyl-7,7,9,9-tetramethyl-1-oxa-3,8-diaza-4-oxo-spiro[4.5]decane 2,2,4,4-tetramethyl-7-oxa-3,13-diaza-14-oxo-dispiro[5.1.4.2]tetradecane 2,2,4,4-tetramethyl-7-oxa-3,14-diaza-15-oxo-dispiro[5.1.5.2]pentadecane 2,2,4,4-tetramethyl-7-oxa-3,20-diaza-21-oxo-dispiro[5.1.11.2]heneicosane 2,2,7,7,9,9-hexamethyl-1-oxa-3,8-diaza-4-oxo-8-acetyl-spiro[4.5]decane 2,2,4,4-tetramethyl-7-oxa-3,14-diaza-15-oxo-3-acetyldispiro[5.1.5.2]pentadecane 2,2,4,4-tetramethyl-7-oxa-3,20-diaza-21-oxo-3-acetyldispiro[5.1.11.2]heneicosane.

Suitable compounds of the formula IX are, for example, methyl acrylate
ethyl acrylate
n-butyl acrylate
isobutyl acrylate
tert-butyl acrylate
2-ethylhexyl acrylate
octyl acrylate
lauryl acrylate
myristyl acrylate
2-diethylaminoethyl acrylate
methyl methacrylate
ethyl methacrylate
n-butyl methacrylate
isobutyl methacrylate
tert-butyl methacrylate
lauryl methacrylate
cyclohexyl methacrylate
allyl methacrylate
2-ethoxyethyl methacrylate
2-dimethylaminoethyl methacrylate
methyl crotonate
ethyl crotonate
1,4-butanediol diacrylate
1,6-hexanediol diacrylate
2-ethyl-2-hydroxymethyl-1,3-propanediol triacrylate
diethylene glycol diacrylate
pentaerythritol triacrylate
pentaerythritol tetraacrylate
ethylene glycol dimethylacrylate
1,4-butanediol dimethacrylate
1,6-hexanediol dimethacrylate
diethylene glycol dimethacrylate
triethylene glycol dimethacrylate
tripropylene glycol diacrylate
trimethylolpropane trimethacrylate
2,2,6,6-tetramethylpiperid-4-yl acrylate
2,2,6,6-tetramethylpiperid-4-yl crotonate
2,2,6,6-tetramethylpiperid-4-yl methacrylate.

For the process according to the invention an aromatic hydrocarbon which is liquid at room temperature, preferably toluene or xylene, is used as solvent.

As phase transfer catalyst a polyethylene glycol dialkyl ether, a substituted phosphonium salt, for example tetraalkylphosphonium halide, or a substituted ammonium salt, for example tetraalkylammonium halide or trialkylbenzylammonium halide, is preferably added. In particular, triethylbenzylammonium chloride or a tetraalkylphosphonium bromide is added. The quantity is 0.05 to 20, preferably 0.1 to 10, in particular 1 to 10 mol %, referred to the compound of formula VIII.

The compound IX is used in a quantity of 1/n to 10/n, preferably 1/n to 3/n, in particular 1/n to 1.5/n mol, referred to 1 mol of the compound VIII. n has the meaning specified above.

The reaction temperature is 30° to 150°, preferably 50° to 120°, in particular 70° to 120° C.

The reaction is performed in the presence of a basic catalyst. An alkali metal, preferably sodium, which is used in a quantity of 130 mol %, preferably 2 to 10 mole %, referred to the compound VIII, functions as such.

The process according to the invention leads to considerable advantages compared with the prior art. First of all, only a single, industrially easy-to-handle solvent or solvent mixture is used. Surprisingly, the effect of the phase transfer catalyst is that the reaction proceeds substantially more rapidly and in particular more completely, with the result that the compound IX no longer has to be used in manifold excess, but a small excess is satisfactory. Despite this, a higher yield is obtained and the amount of the byproducts is reduced.

The compounds prepared according to the invention [of the formula (I)] are used, in particular, as light stabilizers, for example for polyolefins, in particular polyethylene and polypropylene, ethylene/propylene copolymers, polybutylene, and also polystyrene, chlorinated polyethylene, and also polyvinyl chloride, polyester, polycarbonate, polymethyl methacrylates, polyphenylene oxides, polyamides, polyurethanes, polypropylene oxide, polyacetals, phenol formaldehyde resins, epoxy resins, polyacrylonitrile and corresponding copolymers and ABS terpolymers. The compounds prepared according to the invention are preferably used for stabilizing polypropylene, low-molecular and high-molecular polyethylene, ethylene/propylene copolymers, polyvinyl chloride, polyester, polyamide polyurethanes, polyacrylonitrile, ABS, terpolymers of acrylic ester, styrene and acrylonitrile, copolymers of styrene and acrylonitrile or styrene and butadiene, in particular for polypropylene, polyethylene, ethylene/propylene copolymer of ABS.

The compounds prepared according to the invention can also be used for the stabilization of natural substances, for example rubber, and also for lubricating oils. Moreover, they are suitable also for the stabilization of lacquers.

As lacquers all the types used in industrial lacquering, preferably baking enamels, are possible, as ennumerated in the German Offenlegungsschrift No. 3,149,453.

The introduction of the compounds prepared according to the invention into the materials to be protected takes place by processes known per se, it also being possible for monomers or prepolymers or precondensates to be provided with these stabilizers.

In addition to the compounds of the formula (I), other stabilizers may also be added to the plastic materials. Such other compounds are, for example, antioxidants based on sterically hindered phenols, or costabilizers containing sulfur or phosphorus or a mixture of suitable sterically hindered phenols and compounds containing sulfur and/or phosphorus. Such compounds are, for example, benzofuran-2-one and/or indolin-2-one compounds, sterically hindered phenols such as stearyl β-(4-hydroxy-3,5-di-tert-butylphenyl)propionate, tetrakis[methylene-3(3′,5′-di-tert-butyl-4-hydroxyphenyl)propionate]methane, 1,3,3-tris(2-methyl-4-hydroxy-5-tert-butylphenyl)butane, 1,3,5-tris(4-tert-butyl-3-hydroxy-2,6-dimethylbenzyl)-1,3,5-triazine-2,4,6-(1H,3H,5H)-trione, bis(4-tert-butyl-3-hydroxy-2,6-dimethylbenzyl)diothiol terephthalate, tris(3,5-tert-butyl-4-hydroxybenzyl) isocyanurate, triesters of β-(4-hydroxy-3,5-di-tert-butyl-phenyl)propionic acid with 1,3,4-tris(2-hydroxyethyl)-5-triazine-2,4,6-(1H,3H,5H)-trione, glycol bis[3,3-bis(4′-hydroxy-3-tert-butylphenyl)-butanate], 2,3,5-trimethyl-2,4,6-tris(3,5-di-tert-butyl-4-hydroxybenzyl)benzene, 2,2′-methylene-bis(4-methyl-6-tert-butylphenyl) terephthalate, 4,4-methylene-bis(2,6-di-tert-butylphenol), 4,4″-butylidene-bis-(tert-butyl-m-cresol), 4,4-thio-bis(2-tert-butyl-5-methylphenol), 2,2'-methylene-bis(4-methyl-6-tert-butylphenol). Costabilizers having antioxidative action may also be added, such as, for example, sulfur-containing compounds, for example distearyl thiodipropionate, dilauryl thiodipropionate, tetrakis(methylene-3-hexylthiopropionate)methane, tetrakis(methylene-3-dodecylthiopropionate)methane and dioctadecyl disulfide or phosphorus-containing compounds such as, for example, trinonylphenylphosphite, 4,9-distearyl-3,5,8,10-tetraoxadiphosphaspiroundecane, tris(2,4-tert-butylphenyl) phosphite or tetrakis(2,4-di-tert-butylphenyl)-4,4'-butylphenyl)-4,4'-biphenylenediphosphonite.

The compounds of the formula I and their mixtures mentioned above can be used also in the presence of further additives. These are known per se and belong, for example, to the group of the aminoacryl compounds, of the UV absorbers and light stabilizers such as the 2-(2'-hydroxyphenyl)benztriazoles, 2-hydroxybenzophenones, 1,3-bis(2'-hydroxybenzoyl)benzenes, salicylates, cinnamic acid esters, esters of optionally substituted benzoic acids, sterically hindered amines, oxalic acid diamides.

The quantity used of the compounds prepared according to the invention of the formula I is 0.01–5% by weight for plastic materials, 2 to 80 % by weight for stabilizer concentrates and 0.02–5% by weight for lacquers.

COMPARATIVE EXAMPLE A (Example 1 of German Offenlegungsschrift No. 3,149,453, but without purification)

91.1 g (0.25 mol) of 2,2,4,4-tetramethyl-7-oxa-3,20-diazadispiro[5.1.11.2]heneicosan-21-one and 0.3 g (0.01 mol) of sodium were heated in 91.1 g of dimethyl sulfoxide for 2 h at 120° C. 89.5 g (1 mol) of methyl acrylate were then added dropwise in the course of 10 min and stirred for 5 h at 110° C. The reaction mixture was poured onto ice/water and extracted with ether. The organic phase was dried over magnesium sulfate, filtered off and the solvent distilled off. 100 g of a beige solid with a melting point of 103° C. remained behind as residue.

COMPARATIVE EXAMPLE B

Analogous to Comparative Example A, but with only 25.8 g (0.3 mol) of methyl acrylate. This experiment yielded 65.5 g of a light-colored solid with a melting point of 89° C.

COMPARATIVE EXAMPLE C 91.1 g (0.25 mol) of 2,2,4,4-tetramethyl-7-oxa-3,20-diazadispiro[5.1.11.2]heneicosan-21-one and 0.5 g of sodium were heated in 100 g of toluene at 80° C. 21.6 g (0.25 mol) of methyl acrylate were added dropwise in the course of 30 min. Stirring was continued for 6 h at 80° C. Shaking out was then carried out three times with 100 g of water in each case and the toluene was distilled off from the organic phase. From the product 4 g of 2,2,4,4-tetramethyl-7-oxa-3,20-diazadispiro[5.1.11.2]heneicosan-21-one were still isolated by dissolving and recrystallizing. 89 g of light-colored solid remained with a melting point of 97° C.

EXAMPLE 1

The procedure was in accordance with Comparative Example C, but 5 g of triethylbenzylammonium chloride were additionally added. In this case no residue of 2,2,4,4-tetramethyl-7-oxa-3,20-diazadispiro[5.1.11.2]heneicosan-21-one could be isolated. As the end product 104 g of a white solid with a melting point of 104° C. were obtained.

EXAMPLE 2

Procedure as for Comparative Example C, but with the following quantity changes: 25.8 g (0.3 mol) of methyl acrylate and 3 g of triethylbenzylammonium chloride. In this case no residue of 2,2,4,4-tetramethyl-7-oxa-3,20-diazadispiro[5.1.11.2]heneicosan-21-one could be isolated.

As the end product 109 g of a white solid with a melting point of 114° C. were obtained.

EXAMPLES 3 to 5

Procedure as Example 2, but with the following phase transfer catalysts:

| Example | Phase transfer catalyst | End product (g) | Melting point (°C.) |
|---|---|---|---|
| 3 | 5 g triethylbenzylammonium bromide | 96 | 112 |
| 4 | 5 g triethylbenzylammonium chloride | 104 | 108 |
| 5 | 5 g pentaethylene glycol dimethyl ether | 112 | 100 |

EXAMPLES 6 TO 8 AND COMPARATIVE EXAMPLE D

The procedure was as in Comparative Example C, but 76.5 g (0.3 mol) of lauryl acrylate (industrial mixture of approx. 53–55% $C_{12}$ ester and approx. 42–43% $C_{14}$ ester) and also the following quantities of triethylbenzylammonium chloride were used:

| Example | Triethylbenzylammonium chloride in (g) | End product in (g) | Residual content of 2,2,4,4-tetramethyl-7-oxa-3,20-diazadispiro[5.1.11.2]heneicosan-21-one in % by weight |
|---|---|---|---|
| Comp. D | 0 | 151 | 3.8 |
| 6 | 1 | 158 | 2.7 |
| 7 | 3 | 160 | 0.7 |
| 8 | 5 | 146 | 2.3 |

EXAMPLE 9 and 10

The procedure was as in Examples 6 and 8 and Comparative Example D, but with phosphonium salts instead of ammonium salts as phase transfer catalysts.

| Example | Phase transfer catalyst | End product in (g) | Residual content of 2,2,4,4-tetramethyl-7-oxa-3,20-diazadispiro[5.1.11.2]heneicosan-21-one in % by weight |
|---|---|---|---|
| 9 | 3.0 g of tributylhexadecylphosphonium bromide | 160 | 2.6 |
| 10 | 3.8 g of tetrabutylphosphonium | 163 | 0.8 |

-continued

| Example | Phase transfer catalyst | End product in (g) | Residual content of 2,2,4,4-tetramethyl-7-oxa-3,20-diazadispiro[5.1.11.2]heneicosan-21-one in % by weight |
|---|---|---|---|
| | bromide | | |

We claim:
1. A process for the preparation of a 1-oxa-3,8-diaza-4-oxo-spiro[4.5]decane compound of the formula I

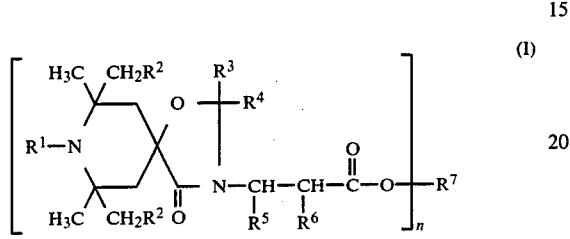

(I)

wherein n is an integer from 1 to 4, $R^1$ is hydrogen, $C_1$–$C_4$ alkyl, benzyl, allyl, $C_2$–$C_{30}$ alkanoyl, $C_3$–$C_{20}$ alkenoyl, $C_7$–$C_{11}$ aroyl, $C_8$–$C_{14}$ arylalkanoyl or $C_8$–$C_{20}$ alkylaryl, $R^2$ denotes hydrogen or $C_1$–$C_4$ alkyl, $R^3$ is hydrogen, $C_1$–$C_{18}$ alkyl, $C_5$–$C_{12}$ cycloalkyl, a phenyl or naphthyl group which may be substituted by chlorine or $C_1$–$C_4$ alkyl, or a $C_7$–$C_{12}$ phenylalkylene group optionally substituted by $C_1$–$C_4$ alkyl, $R^4$ denotes hydrogen, $C_1$–$C_4$ alkyl, $C_5$–$C_{12}$ cycloalkyl, $C_1$–$C_3$ alkenyl substituted by —COOH, carb(-$C_1$–$C_4$ alkoxy) or carbamoyl, a phenyl, naphthyl or pyridyl group which may be substituted by $C_1$–$C_4$ alkoxy or $C_1$–$C_4$ alkyl, or a $C_7$–$C_{12}$ phenylalkyl group which may be substituted by $C_1$–$C_4$ alkyl, or $R^3$ and $R^4$ together with the carbon atom which binds them may form a cycloalkyl group which may be substituted by one to four $C_1$–$C_4$ alkyl groups, or a radical of formula II

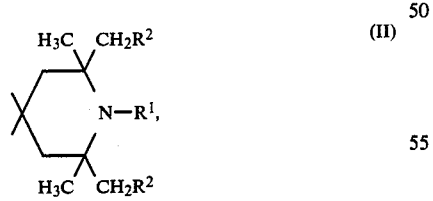

(II)

wherein $R^1$ and $R^2$ have the abovementioned meaning, $R^5$ is hydrogen, methyl, phenyl or carb($C_1$–$C_{21}$ alkoxy), $R^6$ denotes hydrogen or methyl, $R^7$ denotes, for n=1, hydrogen, $C_1$–$C_{21}$ alkyl, $C_2$–$C_{22}$ alkenyl, $C_7$–$C_{18}$ phenylalkyl, $C_5$–$C_{12}$ cycloalkyl, phenyl, naphthyl, $C_7$–$C_{18}$ alkylphenyl, a radical of the formula

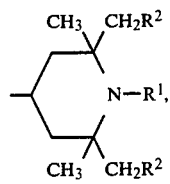

in which $R^1$ and $R^2$ have the meaning specified above, $C_2$–$C_{20}$ alkyl which is interrupted by —O— or

and/or substituted by a radical of the formula III

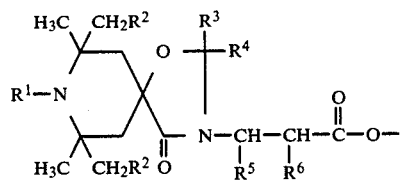

or by $C_1$–$C_{21}$ alkylcarboxyl, $R^1$, $R^2$, $R^3$, $R^4$, $R^5$ and $R^6$ having the meaning specified above and $R^8$ being hydrogen or $C_1$–$C_{10}$ alkyl, $R^7$ denotes, for n=2, straight-chain or branched $C_1$–$C_{30}$ alkylene, $C_2$–$C_{30}$ alkenylene, phenyldialkylene, it being possible for these radicals to be interrupted by —O— or

wherein $R^8$ has the meaning specified above, $R^7$ denotes, for n=3 or 4, a radical of the formulae IV, V, VI or VII

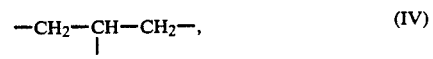 (IV)

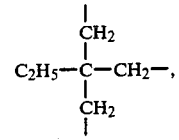 (V)

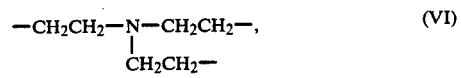 (VI)

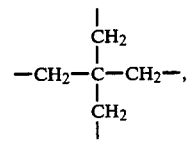 (VII)

by reaction of a compound of the formula VIII

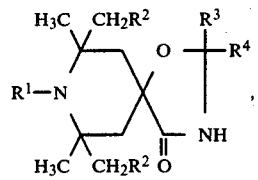 (VIII)

with a compound of the formula IX

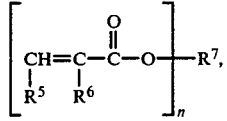 (IX)

where $R^1$, $R^2$, $R^3$, $R^4$, $R^5$, $R^6$ and $R^7$ have the above-mentioned meaning, in an inert solvent at a temperature of 30° to 150° C. in the presence of a basic catalyst, wherein the reaction is performed in the presence of 0.05 to 20 mol %, referred to the compound VIII, of a phase transfer catalyst in an aromatic hydrocarbon which is liquid at room temperature.

2. The process as claimed in claim 1, wherein the aromatic hydrocarbon serving as reaction medium is toluene or xylene.

3. The process as claimed in claim 1, where a substituted phosphonium salt or ammonium salt or a polyethylene glycol dialkyl ether is used as a phase transfer catalyst.

4. The process as claimed in claim 3, wherein a tetraalkyl or tetraalkylbenzylammonium chloride is used as phase transfer catalyst.

5. The process as claimed in claim 3, wherein a tetraalkylphosphonium bromide is used as phase transfer catalyst.

6. A process for the preparation of a 1-oxa-3,8-diaza-4-oxo-spiro[4.5]decane compound of the formula I

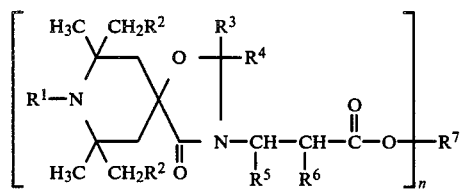 (I)

wherein n is an integer from 1 to 4,
$R^1$ is hydrogen, $C_1$–$C_4$ alkyl, benzyl, allyl, $C_2$–$C_{30}$ alkanoyl, $C_3$–$C_{20}$ alkenoyl, $C_7$–$C_{11}$ aroyl, $C_8$–$C_{14}$ arylalkanoyl or $C_8$–$C_{20}$ alkylaryl,
$R^2$ denotes hydrogen or $C_1$–$C_4$ alkyl,
$R^3$ is hydrogen, $C_1$–$C_{18}$ alkyl, $C_5$–$C_{12}$ cycloalkyl, a phenyl or naphthyl group which may be substituted by chlorine or $C_1$–$C_4$ alkyl, or a $C_7$–$C_{12}$ phenylalkylene group optionally substituted by $C_1$–$C_4$ alkyl,
$R^4$ denotes hydrogen, $C_1$–$C_4$ alkyl, $C_5$–$C_{12}$ cycloalkyl, $C_1$–$C_3$ alkenyl substituted by —COOH, carb(-$C_1$–$C_4$ alkoxy) or carbamoyl, a phenyl, naphthyl or pyridyl group which may be substituted by $C_1$–$C_4$ alkoxy or $C_1$–$C_4$ alkyl, or a $C_7$–$C_{12}$ phenylalkyl group which may be substituted by $C_1$–$C_4$ alkyl, or $R^3$ and $R^4$ together with the carbon atom which binds them may form a cycloalkyl group which may be substituted by one to four $C_1$–$C_4$ alkyl groups, or a radical or formula II

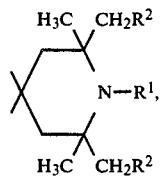 (II)

wherein $R^1$ and $R^2$ have the abovementioned meaning,
$R^5$ is hydrogen, methyl, phenyl or carb($C_1$–$C_{21}$ alkoxy),
$R^6$ denotes hydrogen or methyl,
$R^7$ denotes, for n=1, hydrogen, $C_1$–$C_{21}$ alkyl, $C_2$–$C_{22}$ alkenyl, $C_7$–$C_{18}$ phenylalkyl, $C_5$–$C_{12}$ cycloalkyl, phenyl, naphthyl, $C_7$–$C_{18}$ alkylphenyl, a radical of the formula

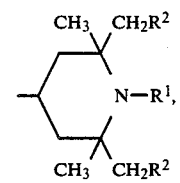

in which $R^1$ and $R^2$ have the meaning specified above, $C_2$–$C_{20}$ alkyl which is interrupted by —O— or

and/or substituted by a radical of the formula III

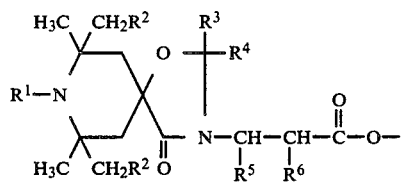

or by $C_1$–$C_{21}$ alkylcarboxyl, $R^1$, $R^2$, $R^3$, $R^4$, $R^5$ and $R^6$ having the meaning specified above and $R^8$ being hydrogen or $C_1$–$C_{10}$ alkyl,
$R^7$ denotes, for n=2, straight-chain or branched $C_1$–$C_{30}$ alkylene, $C_2$–$C_{30}$ alkenylene, phenyldialkylene, it being possible for these radicals to be interrupted by —O— or

wherein $R^8$ has the meaning specified above,
$R^7$ denotes, for n=3 or 4, a radical of the formulae IV, V, VI or VII

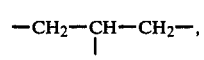 (IV)

-continued

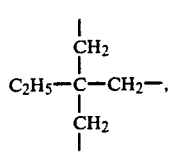
(V)

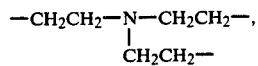
(VI)

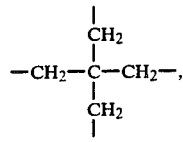
(VII)

said process comprising:

reacting a compound of the formula VIII

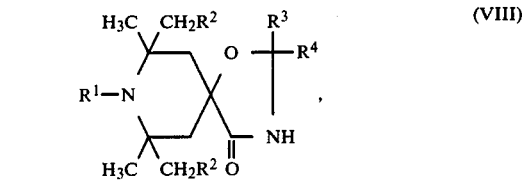
(VIII)

with a compound of the formula IX

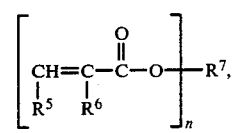
(IX)

where $R^1$, $R^2$, $R^3$, $R^4$, $R^5$, $R^6$ and $R^7$ have the above-mentioned meaning, in a single inert solvent reaction medium consisting essentially of an aromatic hydrocarbon which is liquid at room temperature, at a temperature of 30° to 150° C. in the presence of a basic catalyst, which process additionally comprises including in said reaction medium 0.05 to 20 mole-%, based on the amount of compound VIII, of a phase transfer catalyst.

* * * * *